US00PP13667P29

(12) United States Plant Patent
Takeshita et al.

(10) Patent No.: US PP13,667 P2
(45) Date of Patent: Mar. 18, 2003

(54) CALIBRACHOA PLANT NAMED 'ILLUMINATION BLUE'

(75) Inventors: Daigaku Takeshita, Utsunomiya (JP); Tsutomu Tokita, Omiya (JP); Saori Watanabe, Ujiie (JP); Noboru Onishi, Thousand Oaks, CA (US); Kunihiro Hayashida, Utsunomiya (JP)

(73) Assignees: Kirin Brewery Company, Ltd., Tokyo (JP); Tokia Seed Company, Ltd., Saitama-ken (JP)

( * ) Notice: Subject to any disclaimer, the term of this patent is extended or adjusted under 35 U.S.C. 154(b) by 0 days.

(21) Appl. No.: 10/094,321

(22) Filed: Mar. 8, 2002

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of Calibrachoa plant named 'Illumination Blue', characterized by its cascading and prostrate plant habit; freely branching growth habit; early flowering habit; bright purple-colored flowers with yellow-colored throat; and good weather tolerance.

2 Drawing Sheets

BOTANICAL CLASSIFICATION/CULTIVAR DESIGNATION

Calibrachoa sp. cultivar Illumination Blue.

BACKGROUND OF THE INVENTION

The present Invention relates to a new and distinct cultivar of Calibrachoa plant, botanically known as Calibrachoa sp., and hereinafter referred to by the name 'Illumination Blue'.

The new Calibrachoa is a product of a planned breeding program conducted by the Inventors in Tochigi, Japan. The objective of the breeding program is to create new early flowering Calibrachoa cultivars that have stronger growth and attractive flower coloration.

The new Calibrachoa originated from a cross-pollination made by the Inventors in August, 1997, in Tochigi, Japan, of an unnamed proprietary Calibrachoa selection, not patented, as the female, or seed, parent with the Calibrachoa cultivar Liricashower Blue (erroneously identified as 'Petunia'), disclosed in U.S. Plant Pat. No. 9,885, as the male, or pollen, parent. The new Calibrachoa was discovered and selected by the Inventors as a single flowering plant within the progeny of the stated cross-pollination grown in a controlled environment in Tochigi, Japan, in October, 1998. The selection of this plant was based on its strong plant growth habit and attractive flower coloration.

Asexual reproduction of the new cultivar by terminal cuttings taken in a controlled environment in Saitama-ken, Japan, since January, 1999, has shown that the unique features of this new Calibrachoa are stable and reproduced true to type in successive generations.

SUMMARY OF THE INVENTION

Plants of the cultivar Illumination Blue have not been observed under all possible environmental conditions. The phenotype may vary somewhat with variations in environment such as temperature and light intensity without, however, any variance in genotype.

The following traits have been repeatedly observed and are determined to be the unique characteristics of 'Illumination Blue'. These characteristics in combination distinguish 'Illumination Blue' as a new and distinct cultivar of Calibrachoa:

1. Cascading and prostrate plant habit.
2. Freely branching growth habit.
3. Early flowering habit.
4. Bright purple-colored flowers with yellow-colored throat.
5. Good weather tolerance; tolerant to wind, rain, and low and high temperatures.

Plants of the new Calibrachoa can be compared to plants of the female parent, an unnamed proprietary Calibrachoa selection. In side-by-side comparisons conducted by the Inventors in Tochigi, Japan, plants of the new Calibrachoa differed from plants of the female parent primarily in growth habit as plants of the new Calibrachoa were more prostrate and not as upright as plants of the female parent.

Plants of the new Calibrachoa can be compared to plants of the male parent, the cultivar Liricashower Blue. In side-by-side comparisons conducted by the Inventors in Tochigi, Japan, plants of the new Calibrachoa differed from plants of the cultivar Liricashower Blue in the following characteristics:

1. Plants of the new Calibrachoa had darker green-colored leaves than plants of the cultivar Liricashower Blue.
2. Plants of the new Calibrachoa had larger flowers than plants of the cultivar Liricashower Blue.
3. Plants of the new Calibrachoa and the cultivar Liricashower Blue differed in corolla coloration.

Plants of the new cultivar can also be compared to plants of the cultivar Sunbelkubu, disclosed in U.S. Plant Pat. No.

10,279. In side-by-side comparisons conducted by the Inventors in Tochigi, Japan, plants of the new Calibrachoa differed from plants of the cultivar Sunbelkubu in the following characteristics:

1. Plants of the new Calibrachoa had lighter green-colored leaves than plants of the cultivar Sunbelkubu.

2. Plants of the new Calibrachoa had larger flowers than plants of the cultivar Sunbelkubu.

3. Plants of the new Calibrachoa and the cultivar Sunbelkubu differed in corolla coloration.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photograph may differ slightly from the color values cited in the detailed botanical description which accurately describe the colors of the new Calibrachoa.

The photograph on the first sheet comprises a side perspective view of a typical flowering plant of 'Illumination Blue'.

The photograph on the second sheet comprises a close-up view of a typical flower of 'Illumination Blue'.

DETAILED BOTANICAL DESCRIPTION

In the following description, color references are made to The Royal Horticultural Society Colour Chart except where general terms of ordinary dictionary significance are used. Twenty-centimeter containers with three plants per container were used for the aforementioned photographs and the following description. Plants were grown under conditions which closely approximate commercial production conditions during the winter in Santa Paula, Calif. in a polyethylene-covered greenhouse. Plants used for the photographs and the description were about 14 weeks from planting rooted young plants. During the production period, day temperatures averaged 28° C., night temperatures averaged 21° C., and light levels were about 5,000 footcandles.

Botanical classification: Calibrachoa sp. cultivar Illumination Blue.

Parentage:

*Female, or seed, parent.*—Unnamed proprietary selection of Calibrachoa sp., not patented.

*Male, or pollen, parent.*—Calibrachoa sp. cultivar Liricashower Blue, disclosed in U.S. Plant Pat. No. 9,885.

Propagation:

*Type cutting.*—Terminal vegetative cuttings.

*Time to initiate roots.*—Summer: About 3 days at 25° C. Winter: About 7 days at 20° C.

*Time to produce a rooted young plant.*—Summer: About 21 days at 25° C. Winter: About 23 days at 22° C.

*Root description.*—Fine, fibrous, and white in color.

*Rooting habit.*—Freely branching; dense.

Plant description:

*Form.*—Annual flowering plant; cascading and prostrate plant habit; low mounded; short internodes, dense and bushy appearance.

*Plant height (from soil level to top of plant plane).*—About 16 cm.

*Plant diameter (area of spread).*—About 88 cm.

*Growth rate.*—Relatively rapid.

*Branching habit.*—Freely basal branching, about 6 to 8 basal branches per plant; lateral branches develop at potentially every node; pinching is typically not required.

*Lateral branch description.*—Length: About 48 cm. Diameter: About 3 mm. Internode length: About 1.5 to 2 cm. Orientation: Initially upright, then horizontal. Texture: Pubescent; short, fine hairs. Strength: Strong, but flexible. Color: 146B.

*Foliage description.*—Leaves simple, generally symmetrical. Arrangement: Alternate before flowering, then opposite. Length: About 2.8 cm. Width: About 1 cm. Shape: Narrowly elliptic. Apex: Rounded or broadly acute. Base: Acute. Margin: Entire. Texture, upper surface: Coarse; slightly glandular; slightly pubescent. Texture, lower surface: Coarse; slightly glandular; glabrous. Venation pattern: Pinnate; arcuate. Color: Young foliage, upper surface: 146A. Young foliage, lower surface: 146B. Fully expanded foliage, upper surface: 147A. Fully expanded foliage, lower surface: 147B. Venation, upper surface: 147B. Venation, lower surface: 147C. Petiole length: About 8 mm. Petiole diameter: About 1 mm. Petiole color: 144B.

Flower description:

*Flower type and habit.*—Flowers face upright or outward; solitary and axillary; salverform. Freely flowering habit, about 20 to 22 flowers and flower buds per lateral stem. Flowers persistent. Flowers not fragrant.

*Natural flowering season.*—Spring until frost in the autumn; flowering continuous during this period.

*Time to flower.*—Early flowering; plants begin flowering about 2 weeks after planting.

*Flower longevity on the plant.*—About 2 weeks.

*Flower size.*—Diameter: About 3.4 cm. Tube length: About 3 cm.

*Flower buds (showing color).*—Length: About 2 cm. Diameter: At apex, about 5 mm; at base, about 3 mm. Shape: Roughly oblong. Color: 79C.

*Corolla.*—Arrangement/appearance: Single whorl of five petals, fused into flared trumpet. Petal length from throat: About 1.7 cm. Petal width: About 1.6 cm. Petal shape: Spatulate to flabellate. Petal apex: Rounded with shallow emargination. Petal margin: Entire. Petal texture: Smooth, glabrous; velvety. Color: Petal, when opening, upper surface: 83B; venation, close to 83B. Petal, when opening, lower surface: 87C; venation, close to 87C. Petal, opened flower, upper surface: Brighter than 83B; venation, close to 83B; color does not fade with subsequent development. Petal, opened flower, lower surface: 87B; venation, close to 87B. Flower throat (inside): 5A; venation, close to 185B. Flower tube (outside): 145D; venation, close to 185B.

*Sepals.*—Arrangement/appearance: Single whorl of five sepals fused at base; star-shaped. Length: About 1 cm. Width: About 2 mm. Shape: Narrowly elliptic. Apex: Broadly acute. Margin: Entire. Texture, upper and lower surfaces: Smooth, glabrous. Color: Young and fully expanded sepals, upper surface: 146A. Young and fully expanded sepals, lower surface: 146B.

*Peduncles.*—Length: About 2 cm. Width: About 1 mm. Strength: Moderately strong. Angle: About 45° from stem. Texture: Pubescent. Color: 144A.

*Reproductive organs.*—Stamens: Quantity: Five per flower. Anther shape: Oval. Anther length: Less than 1 mm. Anther color: 18A. Pollen amount: Scarce. Pollen color: 18A. Pistils: Quantity: One per flower. Pistil length: About 9 mm. Stigma shape: Anvil-shaped; curved. Stigma color: 144A. Style length: About 7 mm. Style color: 144C. Ovary color: 150C.

*Seed/fruit.*—Seed and fruit production has not been observed.

Disease/pest resistance: Plants of the new Calibrachoa have not been noted to be resistant to pathogens and pests common to Calibrachoa.

Weather/temperature tolerance: Plants of the new Calibrachoa are tolerant to rain and wind and have been observed to tolerate temperatures from 3 to 35° C.

It is claimed:

1. A new and distinct cultivar of Calibrachoa plant named 'Illumination Blue', as illustrated and described.

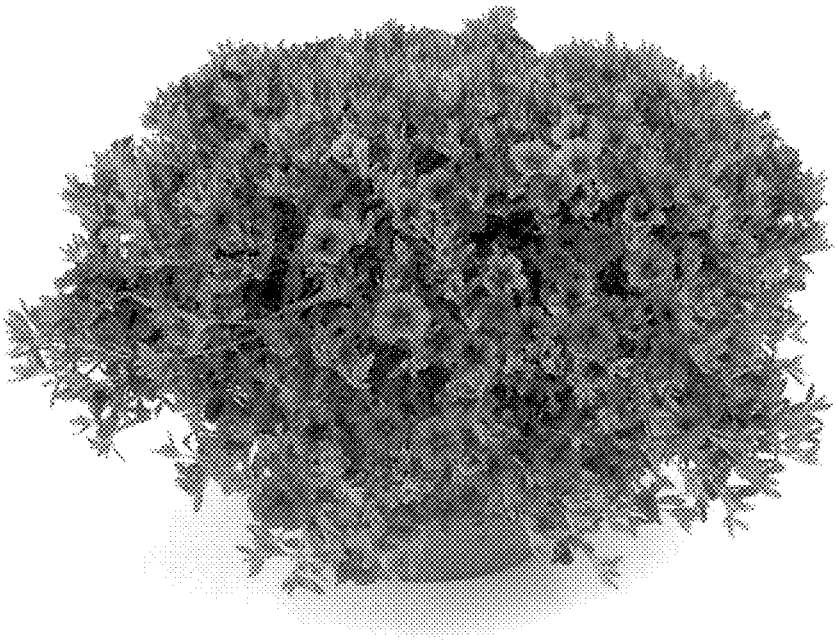

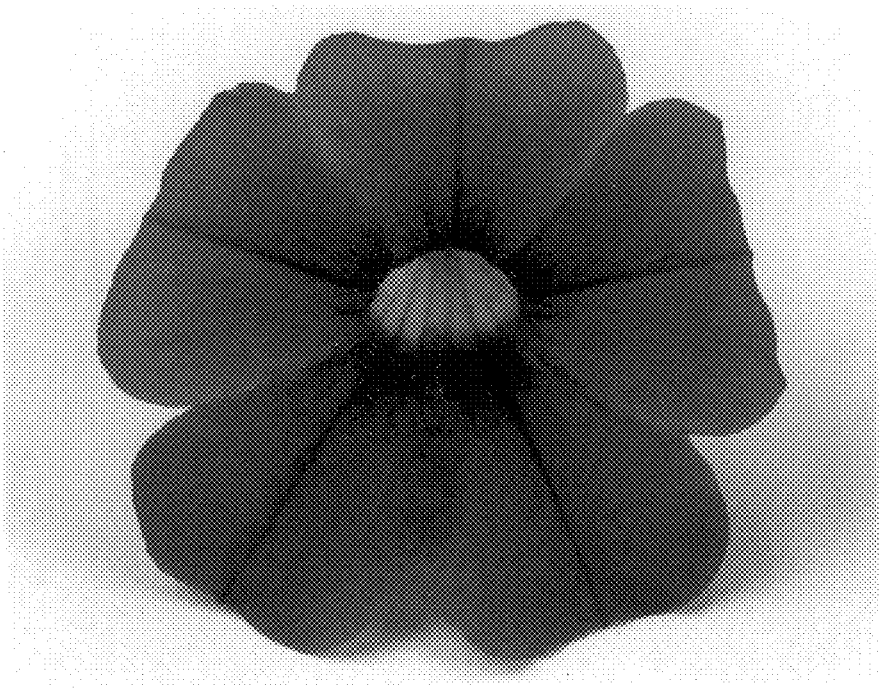

* * * * *